United States Patent [19]

Toledo-Pereyra

[11] 4,186,565
[45] Feb. 5, 1980

[54] PERFUSION SYSTEM FOR ORGAN PRESERVATION

[75] Inventor: Luis H. Toledo-Pereyra, Grosse Pointe Farms, Mich.

[73] Assignee: Henry Ford Hospital, Detroit, Mich.

[21] Appl. No.: 907,878

[22] Filed: May 19, 1978

[51] Int. Cl.² .................... B01F 3/04; A61B 19/00
[52] U.S. Cl. .............................. 62/306; 128/1 R; 435/1
[58] Field of Search ............ 62/306; 128/1 R, DIG. 3; 195/1.7, 127

[56] References Cited

U.S. PATENT DOCUMENTS

| | | | |
|---|---|---|---|
| 3,406,531 | 10/1968 | Swenson et al. | 62/306 |
| 3,545,221 | 9/1970 | Swenson et al. | 62/306 |
| 3,607,646 | 9/1971 | de Roissart | 195/1.7 |
| 3,753,865 | 8/1973 | Belzer et al. | 62/306 |
| 3,777,507 | 12/1973 | Burton et al. | 62/306 |
| 3,914,954 | 10/1975 | Doerig | 62/306 |
| 3,995,444 | 12/1976 | Clark et al. | 128/1 R |

OTHER PUBLICATIONS

"Clinical Kidney Preservation With & Without Continuous Perfusion", by Claes, Blohme & Gelin—published in EDTA Bulletin Jul. 1971.

"Transportable Organ-Perfusion System for Kidney Preservation" by Moberg et al., in *The Lancet*, Dec. 25, 1971.

*Primary Examiner*—Lloyd L. King
*Attorney, Agent, or Firm*—Barnes, Kisselle, Raisch & Choate

[57] ABSTRACT

A portable perfusion system for organ preservation comprising a cart on which a refrigeration unit, a pump unit and a cassette are mounted with the pump and cassette being removable for separate transport. The cassette includes an organ receptacle, a heat exchanger, a membrane oxygenator, a bubble trap and an ice deposit area. The heat exchanger is connected to the refrigeration unit and the perfusate is pumped by a non-pulsatile pump through the heat exchanger to the bubble trap and, in turn, to the organ. An oxygen supply on the cart supplies oxygen to the membrane oxygenator which functions to oxygenate the perfusate.

10 Claims, 3 Drawing Figures

PERFUSION SYSTEM FOR ORGAN PRESERVATION

This invention relates to perfusion systems for organ preservation and particularly for preservation of kidneys.

BACKGROUND AND SUMMARY OF THE IVENTION

In the procurement and transplantation of organs such as kidneys, it is essential to properly preserve the organ, and it has been customary to subject the organ to lower temperatures and a perfusion with a suitable perfusate.

Several methods of kidney perfusion have been used. Folkert O. Belzer, B. Sterry Ashby and J. Englebert Dunphy in *Ann. Surg*, 172:394, 1970, described a system for perfusion of kidneys by hypothermic pulsatile perfusion utilizing a pulsatile pump, a membrane oxygenator, a heat exchanger and a refrigeration unit. The perfusate was supplied by the pump through the heat exchanger and the oxygenator to the organ.

In another system described by A. W. Moberg, E. A. Santiago, R. V. Mason, M. J. Mozes, R. A. Campos and J. S. Najarian, in *The Lancet*, Dec. 25, 1971, a smaller self-contained system was provided utilizing an organ cassette which included an organ chamber, circulating fluid, membrane oxygenator and heat exchanger.

In a third type of system described by G. Claes, I. Blohme and L. E. Gelin in a paper to be published in preceedings from EDTA meeting in Berlin, July 1971, a similar system was provided which included non-pulsatile perfusion, i.e., a pump that did not pulsate.

Among the objects of the present invention are to provide an improved perfusion system which is simpler, more compact and can be utilized portably or otherwise, which does not utilize pulsatile perfusion, and which incorporates an organ cassette that can be interchanged with other systems.

DESCRIPTION

Figure 1:
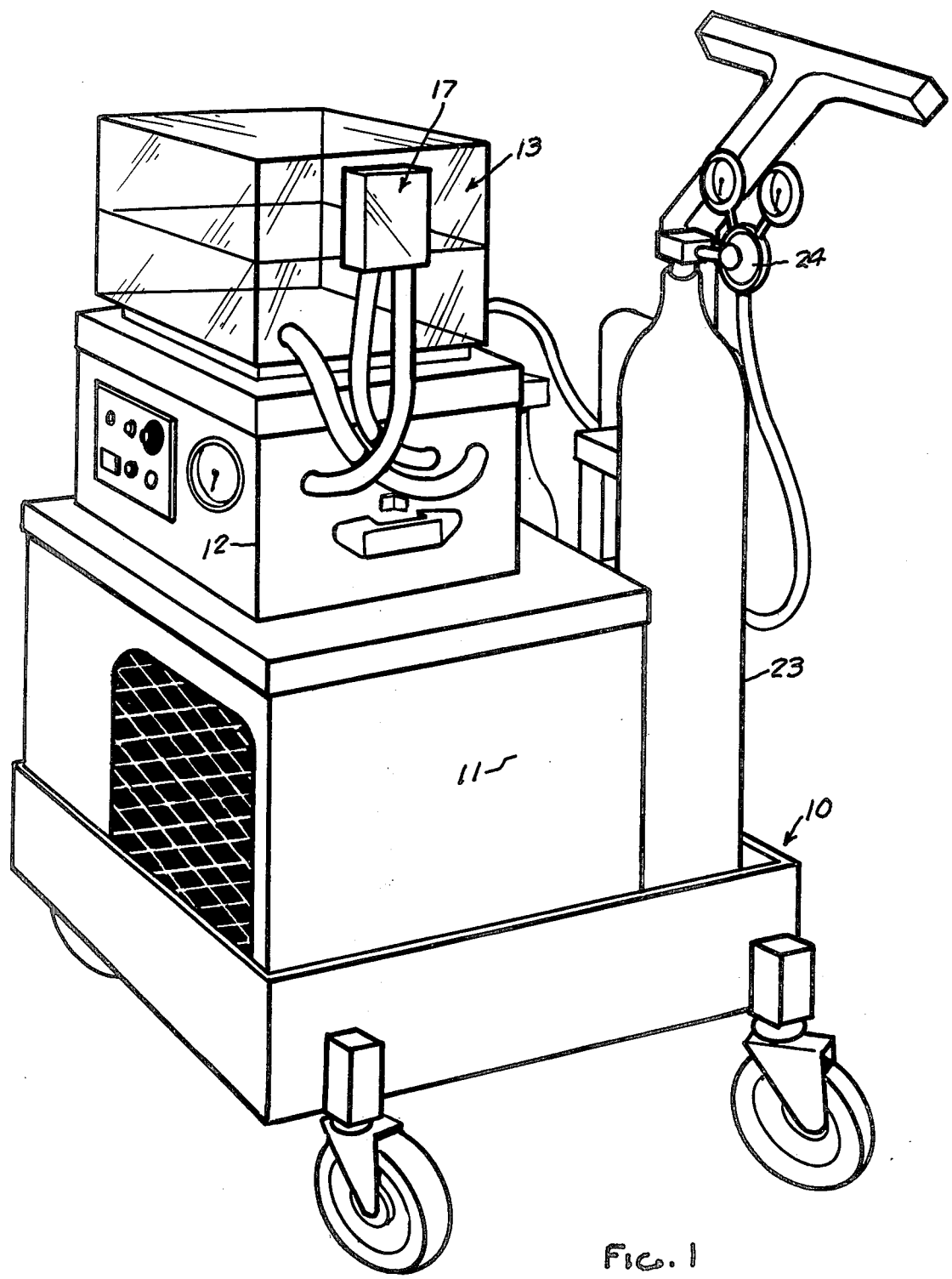
FIG. 1 is a perspective view of an apparatus embodying the invention.
Figure 2:
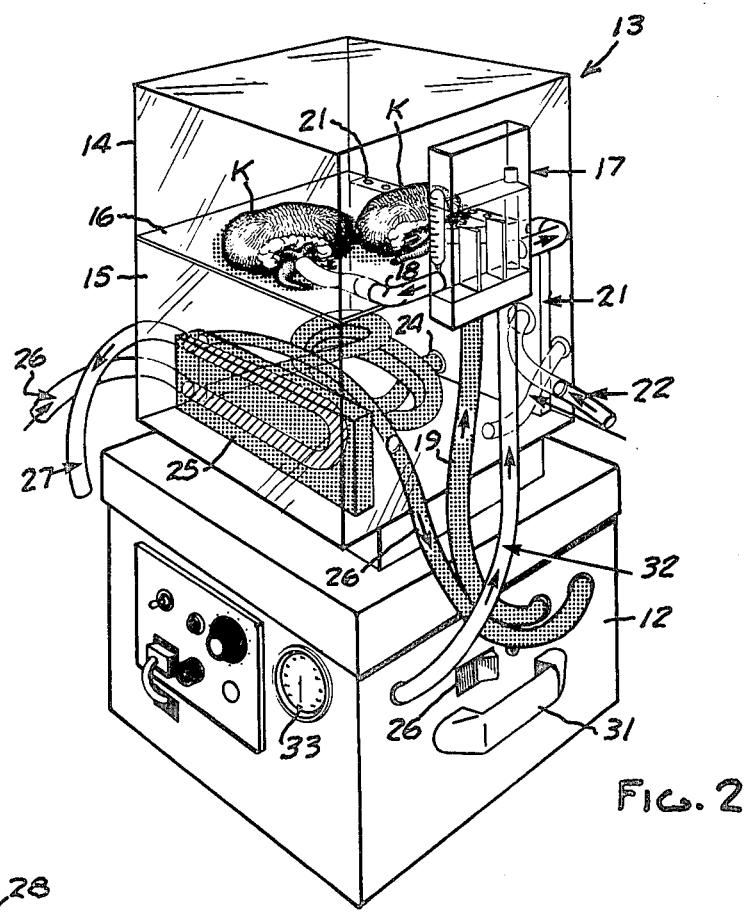
FIG. 2 is a partly diagrammatic view on an enlarged scale of a portion of the system shown in FIG. 1.
Figure 3:
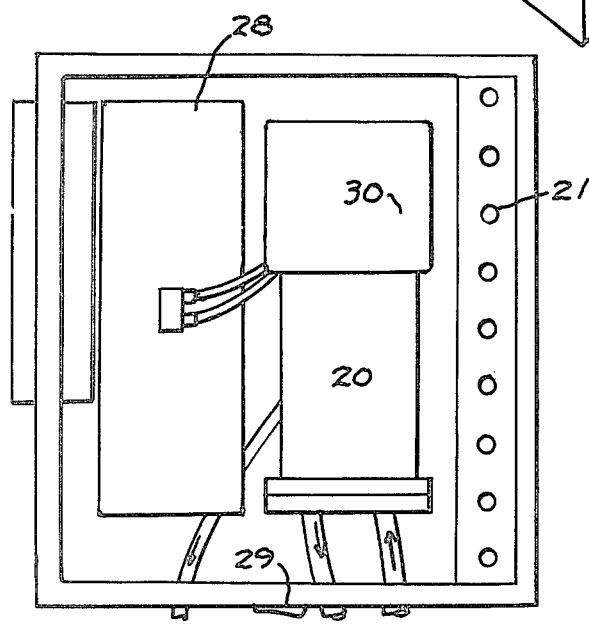
FIG. 3 is a partly diagrammatic plan view of a portion of the system.

Referring to FIG. 1, the perfusion system embodying the invention comprises a wheeled cart 10, a refrigeration unit 11, a pump unit 12 and a cassette 13.

The cassette 13 is preferably made of walls of transparent material such as acrylic plastic and includes an organ receptacle portion 14 removably mounted on a second portion 15. The bottom wall 16 of the portion 14 is adapted to support the organ such as the kidney. A bubble trap 17 is mounted on the side wall of the portion 14 and includes an outlet 18 that extends through the wall and is adapted to be connected to the organ K. The perfusate is supplied to the bubble trap 17 through a line 19 extending from a pump 20 in the pump unit 12. The pump 20 is of the roller type, that is, a non-pulsatile pump. Liquid or perfusate from the kidney K passes through an oxygenator 21 on the wall of the portion 15 of cassette 13 after flowing across the bottom wall 16 and is subjected to oxygen or a mixture of oxygen and carbon dioxide through a line 22 extending from a supply tank or tanks 23 on the cart which have the usual pressure controls 24. The oxygenator is of the well-known membrane type wherein the liquid passes over a membrane and is subjected to the gas. The perfusate after passing through the oxygenator 21 extends to a line 24 that passes to a heat exchanger 25 and, in turn, to an inlet line 26 extending to the pump 20. The refrigeration unit 11 includes inlet and outlet lines 26, 27 extending to the heat exchanger 25 for cooling for the perfusate. A flow regulator is preferably provided on the cart for use in connection with each supply tank 23.

The refrigeration unit 11 includes the usual compressor that is driven electrically so that an electric cord may be used to energize the motor driving the compressor. The pump unit 12 similarly includes an electric cord for driving the motor of the pump. In addition, the pump unit 12 includes a self-contained battery for operating the pump when it is desired to transport the organ. The pump unit 12 thus includes a battery 28, a switching device and converter 29 for providing power from an AC line or the battery 28 to drive the AC-DC motor 30 that in turn drives the pump 20.

It can thus be seen that the perfusion system basically includes a cart 10, a refrigeration unit 11, a pump 12 and a cassette 13, the cassette 13 containing the organ chamber 14, bubble trap 17, heat exchanger 25, and membrane oxygenator 21. When it is desired to transport the organ, ice can be incorporated into the area surrounding the heat exchanger of portion 15 of the cassette 13, the refrigeration lines 26, 27 being disconnected, and the power supply being switched so that the pump is operated by the battery. Then by merely grasping handles 31 on the pump unit, the pump unit 12 and cassette 13 can be transported. Where it is desired to connect the cassette to other systems, the cassette 13 can be disconnected from the pump unit. For purposes of monitoring the pressure of the perfusate, a line 32 extends from a pressure gauge 33 in the pump unit to above the level of the liquid in the bubble chamber 17.

The apparatus described has been found to produce excellent results. Thus, when canine kidneys were perfused for 48 to 72 hours, the viability parameters (flow, pressure, oxygen tension, lactic acid, pH) were within normal limits. Minimal weight gain was observed after preservation. After transplantation, the kidneys perfused for 48 hours showed a good vascular perfusion throughout the kidney as well as good urine output. After transplantation, the kidneys perfused for 72 hours functioned but did not show as good results as the kidneys perfused for 48 hours.

Typical operating conditions were: pressure of perfusate of cryoprecipitated plasma, 25–30 mm. of mercury; rate of flow of perfusate, 150 mil/min.; oxygen flow, 1 liter/min.; $CO_2$ flow 8 mil/min.; pH 7.38–7.4; and average kidney weight 50 grams.

Although the apparatus has been described in connection with the preservation of kidneys, it can also be used in the preservation of other organs such as hearts, pancreases and livers.

I claim:

1. A perfusion system for organ preservation comprising
   a wheeled cart,
   a refrigeration unit on said cart having coolant inlet and outlet lines,
   a pump unit removably mounted on said cart and having pump inlet and outlet lines, and a cassette removably mounted on said cart and including an organ receptacle for receiving the organ, a heat exchanger, a bubble trap having an inlet line and an outlet line, a membrane oxygenator having an inlet and an outlet line, and an ice deposit area, said heat exchanger being connected to the inlet and outlet lines of the refrigeration unit and having perfusate inlet and outlet lines connected to the outlet line of the said oxygenator and the inlet line of the pump unit, said bubble trap having an inlet line connected to the outlet line of said pump unit, said outlet line of said bubble trap being adapted to be connected to the organ, said oxygenator having a gas inlet line, and a gas tank on said cart connected to said gas inlet line.

2. The combination set forth in claim 1 wherein said organ receptacle is removable from the remainder of said cassette for individual transport of the organ.

3. The combination set forth in claim 1 wherein said cassette has transparent walls.

4. A perfusion system for organ preservation comprising a refrigeration unit having coolant inlet and outlet lines, a pump unit removably mounted on said refrigeration unit and having pump inlet and outlet lines, and a cassette removably mounted on said pump unit and including an organ receptacle for receiving the organ, a heat exchanger, a bubble trap having an inlet line and an outlet line, a membrane oxygenator having an inlet and an outlet line, and an ice deposit area, said heat exchanger being connected to the inlet and outlet lines of the refrigeration unit and having perfusate inlet and outlet lines connected to the outlet line of said oxygenator and the inlet line of the pump unit, said bubble trap having an inlet line connected to the outlet line of said pump unit, said outlet line of said bubble trap being adapted to be connected to the organ, said oxygenator having a gas inlet line for connection to a gas tank.

5. The combination set forth in claim 4 wherein said organ receptacle is removable from the remainder of said cassette for individual transport of the organ.

6. The combination set forth in claim 4 wherein said cassette has transparent walls.

7. The system set forth in claim 1 wherein said pump is a non-pulsatile pump.

8. The system set forth in claim 7 wherein said pump unit includes self-contained power means for operating said pump.

9. The system set forth in claim 4 wherein said pump is a non-pulsatile pump.

10. The system set forth in claim 9 wherein said pump unit includes self-contained power means for operating said pump.